(12) United States Patent
Häusler et al.

(10) Patent No.: US 8,845,573 B2
(45) Date of Patent: Sep. 30, 2014

(54) IMPLANTABLE ACCESS FOR REMOVAL AND/OR RETURN OF FLUIDS

(75) Inventors: Rudolf Häusler, Bollingen (CH); Felix Frey, Kriechenwil (CH); Christof Stieger, Bern (CH); Andreas Arnold, Bern (CH); Stefan Farese, Solothurn (CH); Dominik Uehlinger, Kerzers (CH)

(73) Assignee: Universitaet Bern, Bern (CH)

( * ) Notice: Subject to any disclaimer, the term of this patent is extended or adjusted under 35 U.S.C. 154(b) by 371 days.

(21) Appl. No.: 12/859,370

(22) Filed: Aug. 19, 2010

(65) Prior Publication Data

US 2011/0034852 A1    Feb. 10, 2011

Related U.S. Application Data

(63) Continuation of application No. PCT/EP2009/051967, filed on Feb. 19, 2009.

(30) Foreign Application Priority Data

Feb. 21, 2008    (EP) ..................... 08151751

(51) Int. Cl.
| | | |
|---|---|---|
| *A61M 37/00* | (2006.01) | |
| *A61M 31/00* | (2006.01) | |
| *A61B 5/00* | (2006.01) | |
| *A61M 39/02* | (2006.01) | |
| *A61M 1/36* | (2006.01) | |

(52) U.S. Cl.
CPC ... *A61M 39/0247* (2013.01); *A61M 2039/0276* (2013.01); *A61M 2039/0282* (2013.01); *A61M 2039/027* (2013.01); *A61M 1/3653* (2013.01); *A61M 2039/025* (2013.01); *A61M 2039/0261* (2013.01)
USPC ................. 604/9; 604/8; 604/507; 604/508; 604/513

(58) Field of Classification Search
CPC .................. A61M 39/0247; A61M 2039/025; A61M 2039/0261; A61M 2039/0258; A61M 2039/0273; A61M 2039/0279; A61M 2039/0288
USPC .................. 604/8, 9, 27, 504, 507, 508, 513; 433/229
See application file for complete search history.

(56) References Cited

U.S. PATENT DOCUMENTS 3,626,938 A * 12/1971 Versaci ......................... 604/122
5,990,382 A   11/1999 Fox (Continued)

FOREIGN PATENT DOCUMENTS

| WO | 8907467 A1 | 8/1989 |
|---|---|---|
| WO | 9749438 A1 | 12/1997 |
| WO | 2007051339 A1 | 5/2007 |

OTHER PUBLICATIONS

International Search Report for PCT/EP2009/051967, dated Aug. 24, 2009.

*Primary Examiner* — Leslie Deak (74) *Attorney, Agent, or Firm* — Pearne & Gordon LLP (57) ABSTRACT

Implantable access device for removal and/or return of fluids to a patient, comprising a casing attached to an internal conduit to be connected with a lumen of the patient; a connector attached at the casing and connected to an external conduit, and arranged for attachment of an extracorporeal lumen to the device; and an actuator unit within the casing to selectively allow or block the fluid communication between the internal conduit and the external conduit; the device further comprising a fixation unit integrated in or attached at the casing arranged for fixation of the device to a bone of the patient; wherein the fixation unit extends axially along the longitudinal axis of the device. The disclosed access device can be used for high volume removal and/or return of blood or other fluids from the patient.

20 Claims, 10 Drawing Sheets

(56) References Cited

U.S. PATENT DOCUMENTS

| | | | |
|---|---|---|---|
| 6,524,273 B2 * | 2/2003 | Kawamura | 604/93.01 |
| 6,758,832 B2 * | 7/2004 | Barbut et al. | 604/113 |
| 6,840,919 B1 * | 1/2005 | Håkansson | 604/175 |
| 7,513,883 B2 * | 4/2009 | Glenn | 604/8 |
| 8,075,630 B2 * | 12/2011 | Ricci et al. | 623/23.74 |
| 2005/0256540 A1 * | 11/2005 | Silver et al. | 607/3 |

* cited by examiner

IMPLANTABLE ACCESS FOR REMOVAL AND/OR RETURN OF FLUIDS

FIELD OF THE INVENTION

The present invention relates to an implantable access for removal and/or return of fluids to a patient, according to the preamble of claim 1. The implantable port is usable for establishing temporary access to an animal's (including human) blood vessels, an organ, a body lumen or cavity or any combination thereof for the purpose of hemodialysis, drug delivery, nutrition delivery, urinary catheterism or any other supply or removal of fluids.

DESCRIPTION OF RELATED ART

Access to a patient's lumen can be established by a variety of temporary and permanently implanted devices. However, despite several types of lumen access ports and devices proposed over recent years, body lumen access remains one of the most problematic areas in the treatment of patients requiring long-term access. Most simply, temporary access can be provided by the direct percutaneous introduction of a needle through the patient's skin and into a blood vessel. While such a direct approach is relatively straightforward and suitable for applications such as intravenous feeding, short term intravenous drug delivery and other applications which are limited in time, they are not suitable for hemodialysis and other extracorporeal procedures that must be repeated periodically and often for the patient's lifetime.

Haemodialysis patients commonly undergo a placement of one of the two, or both, widely accepted long-term vascular access options during the term of their treatment. It is estimated that 50% of hospitalization time of haemodialysis patients is related to problems of access to the vascular system of the human body.

On the one hand, WO 2005/023336 discloses a surgical placement of an arteriovenous synthetic graft connecting a patient's adjacent peripheral artery and vein to divert some of the arterial blood flow through the graft. The other is an arteriovenous fistula, a direct surgical connection between adjacent artery and vein with no synthetic conduit used. In both cases, the blood circulation is accessed with two needles inserted through the skin into either the synthetic graft in the former case, or the venous portion of an arteriovenous fistula in the latter scenario. Needle stick injuries and infections contribute to the loss of these types of accesses.

WO 2007/008197 and U.S. Pat. No. 6,007,516 propose implantable ports to achieve permanent access to a body lumen. Such a port includes a chamber mounted on an access region, such as a septum, and the chamber is attached to an implanted catheter which in turn is secured to a body lumen. The port is fixed subcutaneously to soft tissue. Such systems suffer from a number of problems, such as haematoma, thromboses, stenosis, dilatations, and infections.

U.S. Pat. No. 6,007,516 by Burbanks et al. describes a subcutaneous housing with an attached conduit to blood vessels or another body lumen or cavity. An actuator mechanism is provided with a linkage that opens a valve in the port in response to percutaneous insertion of a needle into the access port. However, the technology probably suffers from a number of practical problems, such as potential displacement, reactions and/or alterations of the surrounding tissue, and the fact that the port is still dependent on the repeated insertion of needles.

US 2006/0047249 by Shubayev and Elyav proposes a percutaneous vascular access system. This system consists of a cylindrical device body having a pair of hollow nipples extending from the exterior to the interior and a rotatable inner core with two positions to open and close the connections. However, the fixation of such a device to the skin or other soft tissue of the body, i.e. as a tissue anchor according to US 2006/0047249, raises a number of problems, such as the danger of displacement during use caused by body movements or exposure to mechanic stress. Moreover, it is commonly known that such systems have a high infection risk.

US 2007/008197 by Langenbach is a transcutaneous access to existing blood vessels or a fistula. It consists of a connecting member for attaching a valve to a fistula as well as a grommet. The device is fixed to the skin and allows the transfer of fluid from or to a fistula or blood vessel. Again, this system shares the problem of sensitivity to mechanic stress and infections.

U.S. Pat. No. 5,911,706 describes an implantable vascular access for removal and/or return of fluids to a patient. The skin has to be perforated every time when vascular access is needed. The casing of this access is subcutaneously fixed on soft tissue.

Bone implanted access devices have also be proposed. For example, WO 2006/004279 discloses a port system for delivering insulin to an implanted insulin pump. This port system comprises a delivery device and a matching filling device. The delivery device comprises an implant, preferably a tooth implant, in which a continuous channel with a valve is formed, and an adjoining catheter.

US 2005/256540 discloses an implantable access device comprising a first portion extending into the mouth external to a tooth-supporting bone; a second portion for being embedded in the tooth-supporting bone; an opening extending along the implant from the first portion to the second portion; an internal conduit in communication with the opening, and extending from the implant to the site in the body. The device is however destined to be implanted only into a tooth-supporting bone and comprises only one external and internal fluid canal.

WO 2007/051339 concerns an access port comprising a central cylindrical portion, and external and internal canal communicating through a valve. Here, the access port contains only one fluid canal and is destined to be implanted in a tooth-supporting bone.

WO 97/49438 concerns an implantable access device for removal and/or return of fluids, such as insulin, chemotherapeutic agents, etc., and comprising a central body, an internal conduit, a connector, an external conduit, and an actuator unit allowing for the fluid communication between the internal and external conduits. The device is fixed on a bone using a fixation plate, extending perpendicular with the casing.

A device comprising the features of the preamble of claim 1 is known from US 2006/0047249.

BRIEF SUMMARY OF THE INVENTION

An object of the invention is therefore to propose an implantable access device which overcomes at least some limitations of the prior art.

Another object of the invention is to provide an implantable access device for removal and/or return of fluids to a patient that can be fixed in a permanent fashion to the patient with reduced risk of infection, and that can be used for high volume removal and/or return of fluids from the patient.

According to the invention, these aims are achieved by means of an implantable access device for removal and/or return of fluids to a patient, being an animal or human, comprising a casing attached to an internal conduit to be connected with a lumen of the patient; a connector attached at the casing and connected to an external conduit, and arranged for attachment of an extracorporeal lumen to the device; and an actuator unit within the casing to selectively allow or block the fluid communication between the internal conduit and the external conduit; the device further comprising a fixation unit integrated in or attached at the casing arranged for fixation of the device to a bone of the patient; wherein the fixation unit extends axially along the longitudinal axis of the device, and wherein the internal conduit comprises two or more tube lines for a predetermined flow direction and the external conduit comprises two or more separate access lines for a predetermined flow direction; the tube lines exiting the casing in a direction substantially parallel with the longitudinal axis of the device.

In an embodiment, the fixation unit is a single, preferably central, bone screw.

In another embodiment, the bone screw is a hollow bone screw accommodating the portion of the internal conduit near the casing.

In yet another embodiment, at least a portion of the casing is used as a fixation unit. The fixation unit can be a threaded structure, a roughened or three-dimensional structure, provided on the lower portion of the casing.

In yet another embodiment, the portion of the internal conduit near the casing is attached essentially perpendicular to said longitudinal axis of the device.

The present invention provides bone anchored access ports that may be used for high volume removal and/or return of blood or other fluids from the animal's (including human) body undergoing an extracorporeal blood therapy such as hemodialysis, hemofiltration, hemodiafiltration, apheresis, or a drug therapy, or a non-oral nutrition, or urinary catheterism or the like. Particular features of the present invention are the fixation method, as well as constant percutanous access to the body lumen. At least one part of the device is intended to be anchored to a section of the animal skeleton, such as the bony part of mastoid, hip, sternum, clavicula or others. The port contains at least one valve and one plug, which facilitates exchange of fluids when open and inhibits leakage of fluid when closed. Extracorporeal lumen can be connected or disconnected without loss of liquid and undesired aspiration of air.

Although the bone anchored access ports are particularly useful for establishing vascular access, they will also be useful for accessing other body lumens and cavities, such as the peritoneal cavity and the like.

BRIEF DESCRIPTION OF THE DRAWINGS

The invention will now be described in exemplary embodiments with reference to the drawings:

FIG. 3B' is a variant of the embodiment of FIG. 3B;

FIG. 3.1C' is a variant of the embodiment of FIG. 3C;

FIG. 3.2C' is another variant of the embodiment of FIG. 3C;

DETAILED DESCRIPTION OF POSSIBLE EMBODIMENTS OF THE INVENTION

Figure 1:
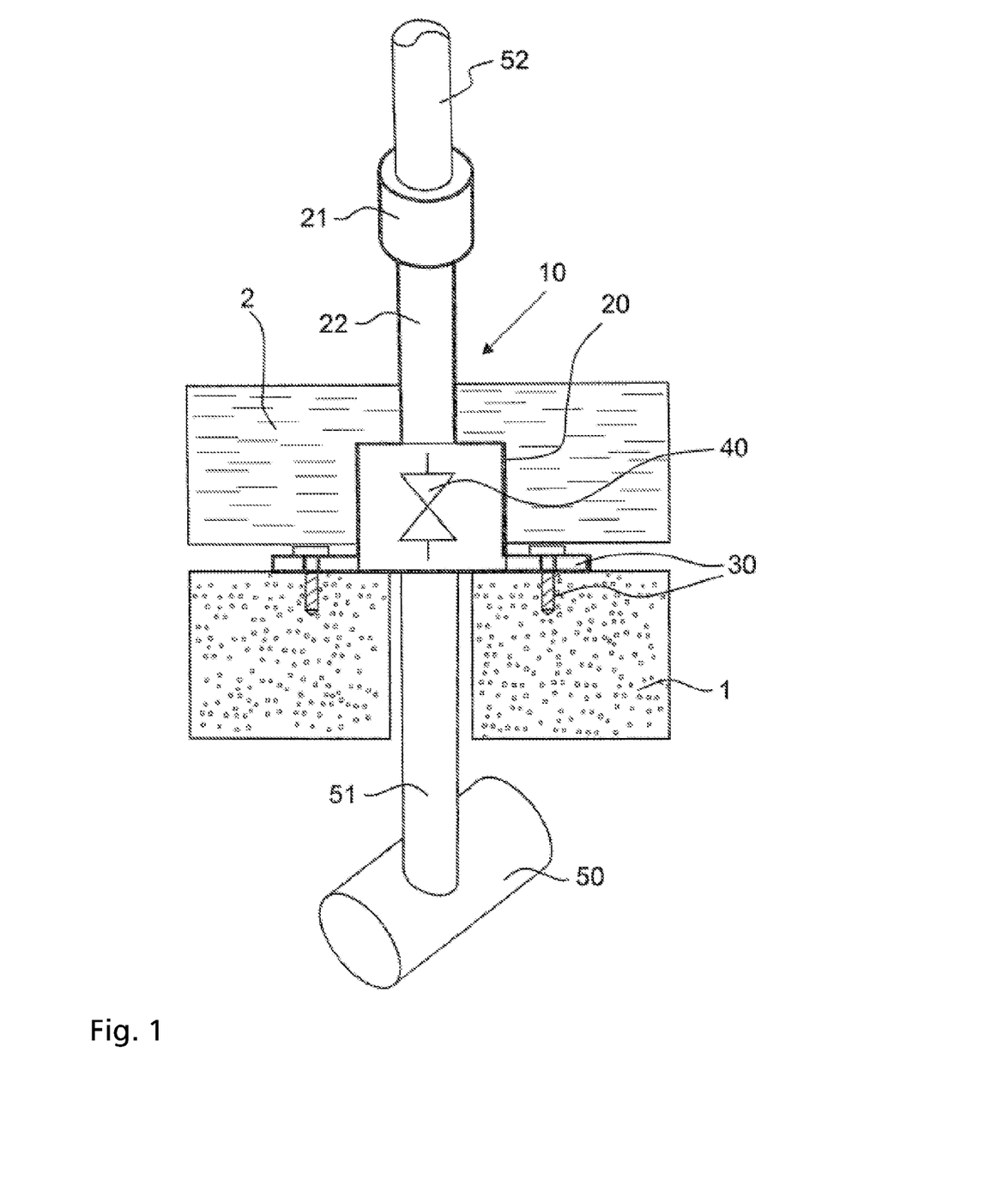
FIG. 1 is a schematical view of the functional parts of the bone anchored access port according to the invention.

FIG. 1 illustrates a schematical view of the functional parts of the bone anchored access port 10, according to the invention. It provides methods and apparatus for facilitating access to a body lumen or organ 50 of an animal. Such exemplary body lumens include blood vessels, the bladder, the digestive system, organs like heart, pancreas, liver, kidney, lung, and brain, the peritoneal cavity, etc. The device is particularly useful for accessing blood vessels, including both arterial and venous, but it should be appreciated that the invention applies to various organs, body lumens and cavities where selective access might be desired. The physical access to lumen 50 is made through a tubing serving as internal conduit 51, which is insertable into the lumen according to known procedures.

The access port, according to the invention, consists of a casing 20 having a fixation device, or fixation unit, designated with the general reference numeral 30. Said fixation unit can comprise a base plate with corresponding screw or being realized as a screw. The casing 20 comprises a connector 21 to an external conduit 52. As can be seen in FIG. 1, the casing 20 is transcutaneous. Casing 20 and fixation unit 30 can be made from one part or can be produced in two or more elements assembled together. Here, the fixation unit is intended to fix, or anchor, the access port to a bone of a patient (being an animal or human).

The casing 20 comprises an actuator unit, e.g. a valve unit, 40. Said valve unit 40 is connected on the one hand to said internal conduit 51 and on the other hand, via external conduit 22 and connector 21, to an extracorporeal lumen or tubing 52.

The base plate 30, according to FIG. 1, is permanently anchored to the bone 1 such as mastoid, hip, clavicula, sternum or any other section of the skeleton. Anchoring is performed with screws, pins, wires, non-absorbable threads, cement or any other suitable fixation means. An external conduit 22, and/or the casing 20 itself, permanently perforates the skin 2 in order to provide direct access to the connector 21 from extracorporeal lumen 52, such as from a haemodialysis system, repositories for drug or nutrition delivery, bags for urinary catherism and the like. The connector 21 can be a pipe coupling, such as a threaded coupling, basquill lock and the like, and connects and seals the external conduit 22 with the conduit of the extracorporeal lumen 52. The pipe coupling 21 may be integrated in the casing 20. The internal conduit 51 can be flexible and can pass subcutaneously or through the bone before penetrating soft tissue and/or the designated lumen 50. The distal tip of the internal conduit 51 is connected to a body lumen by simple perforation, sewing, gluing and the like.

Figure 2:
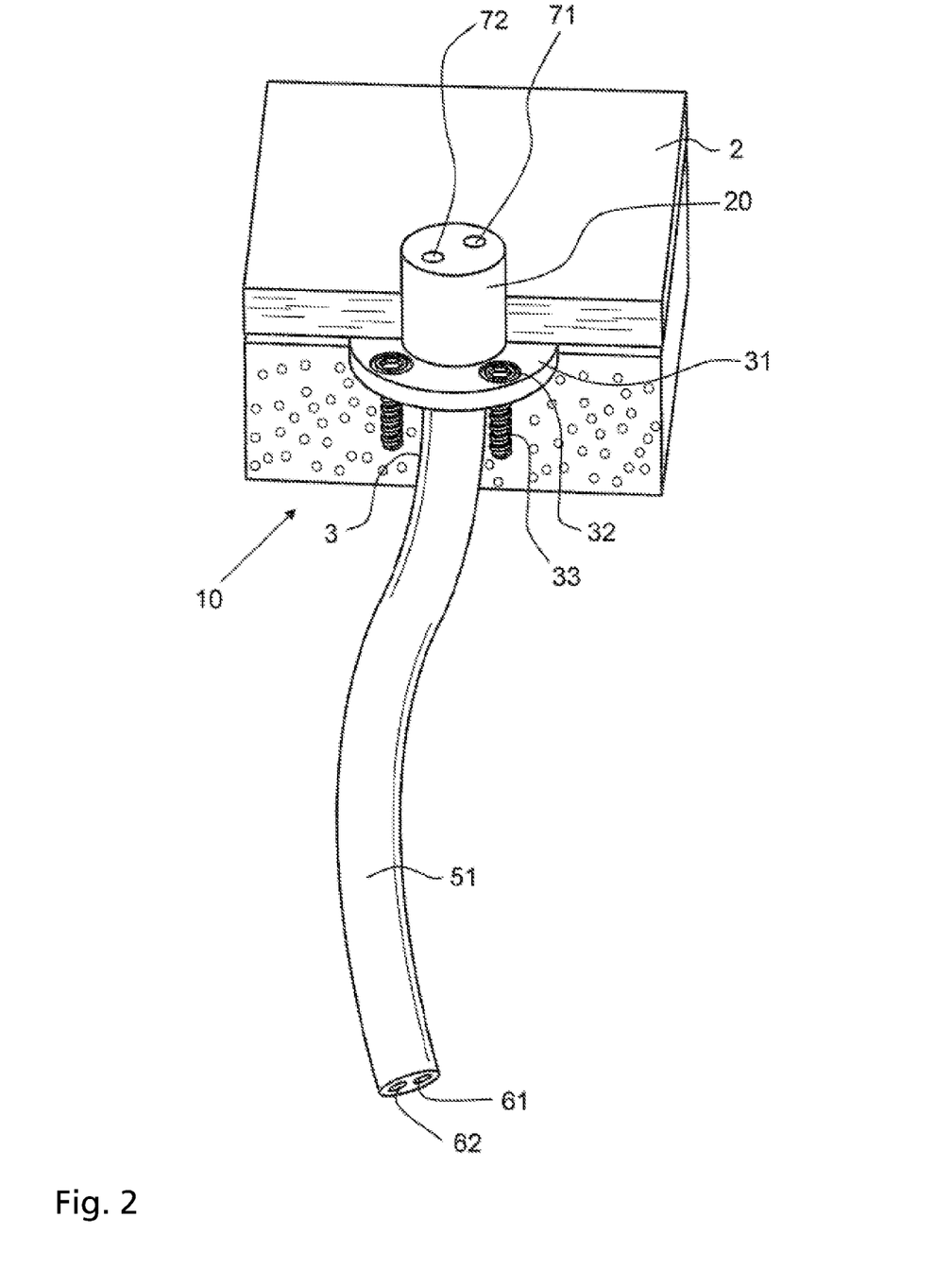
FIG. 2 is a perspective view of an implanted, bone anchored access port with two separate tube lines according to a first embodiment of the invention.
Figure 4A:
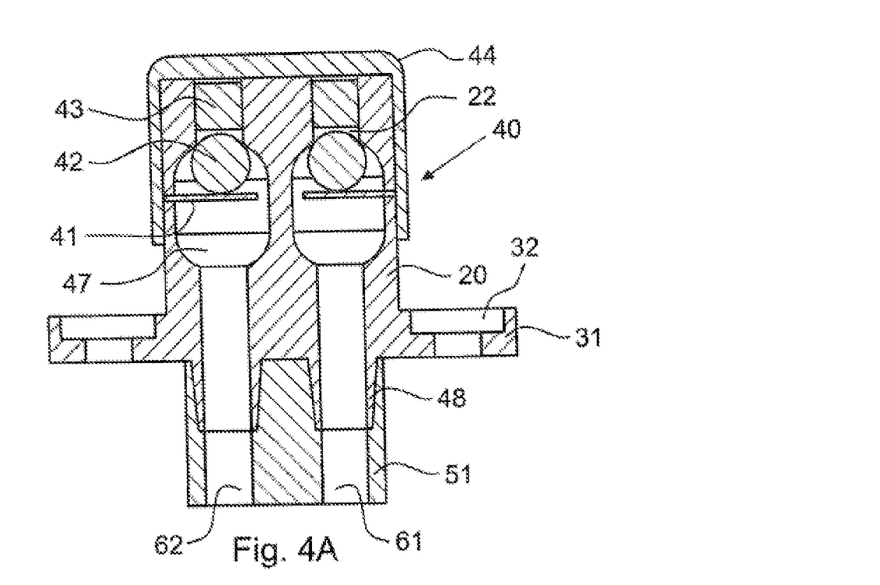
FIG. 4A is a cross section for one embodiment of the valve part of the bone anchored port according to FIG. 2 with a ball valve in closed valve position.
Figure 4B:
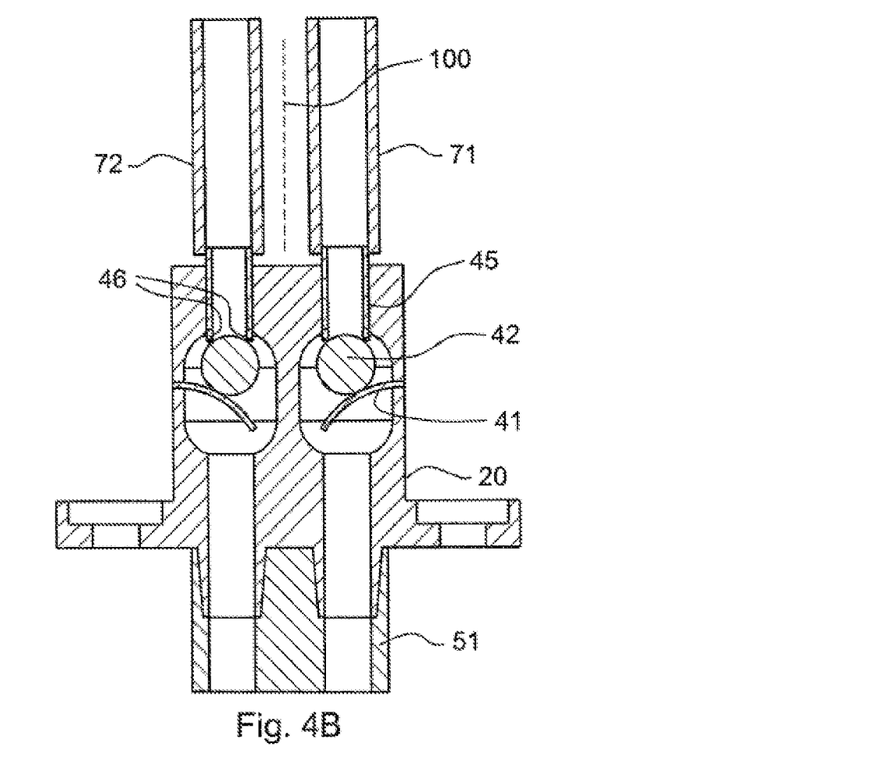
FIG. 4B is a cross section as in FIG. 4A with the ball valve in open valve position.
Figure 5A:
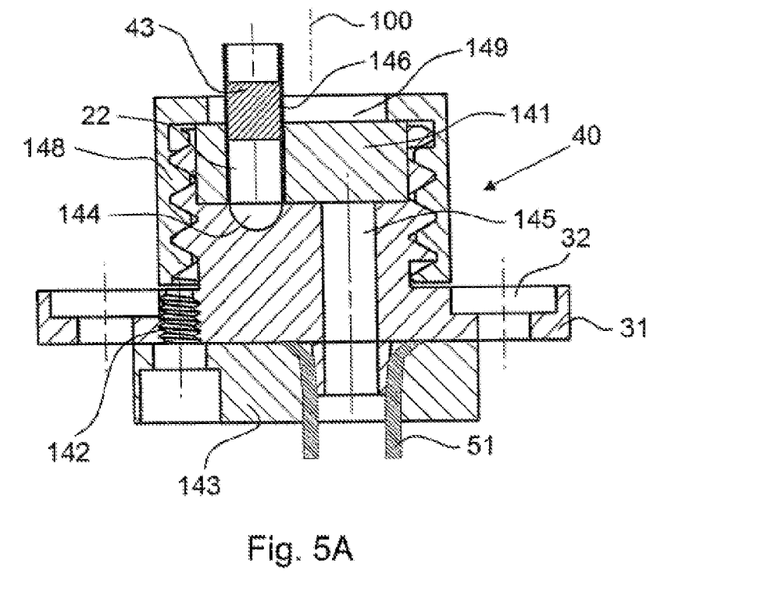
FIG. 5A is a cross section for another embodiment of the valve part of the bone anchored port according to FIG. 2 with a disk valve in closed valve position.
Figure 5B:
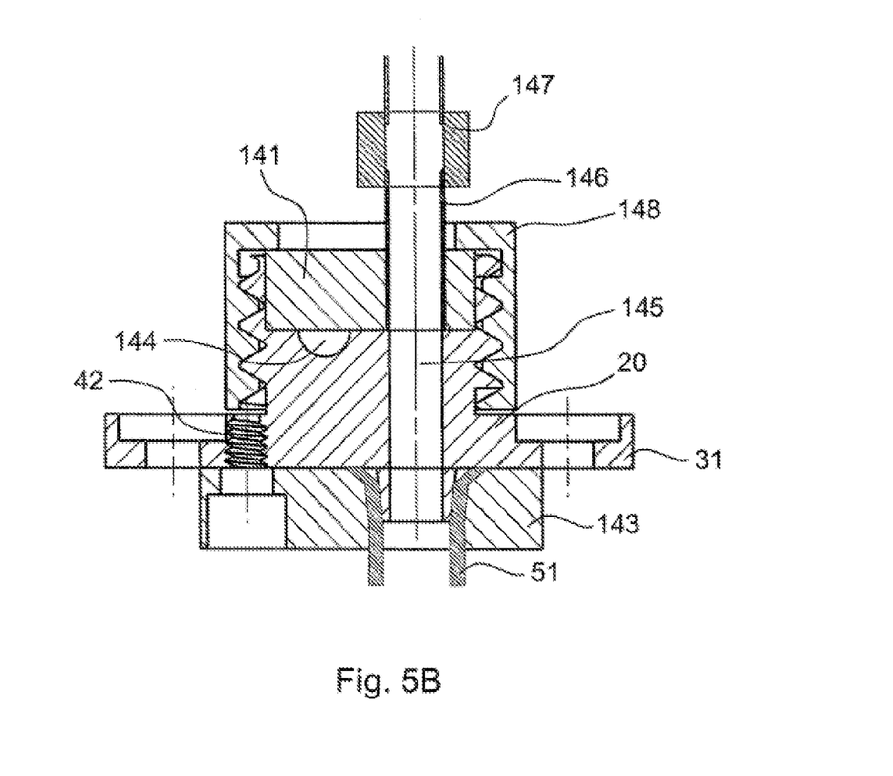
FIG. 5B is a cross section as in FIG. 5A with the disk valve in open valve position.

FIG. 2 is a perspective view of an implanted bone anchored access port 10 with two separate tube lines 61, 62, according to a first embodiment of the invention. Identical or similar features receive the same reference numerals throughout the specification. The bone anchored access port 10 comprises two parallel access lines 71, 72. In this embodiment, each access line 71 or 72 has in sequence a single connector 21, a single actuator mechanism 40, and a single internal tube line 61 and 62, respectively. Although both conduits 61 and 62 are packaged in a single tube 51 they could be assembled in two independent tubes. Actuator mechanism 40 can be realized as shown in FIGS. 4 and 5.

Access port 10, according to FIG. 2, comprises a plate 31 connected with the casing 20. Plate 31 comprises a number of, e.g. four, through going holes 32. Said holes 32 allow for the introduction of fixation screws 33 oriented in parallel with the connector part of the internal conduit 51 near the casing 20 and surrounding it. The internal conduit 51 is thus passing in a hole 3 in the bone 1 provided therefore. Beside such a parallel orientation the screws 33 can also be oriented in a different angle such as 45 degrees. The holes 32 can be used for accommodating sewing threads or an equal number of bone pins as fixation means 33. It is also possible to fill the holes 32 with cement.

Figure 3:
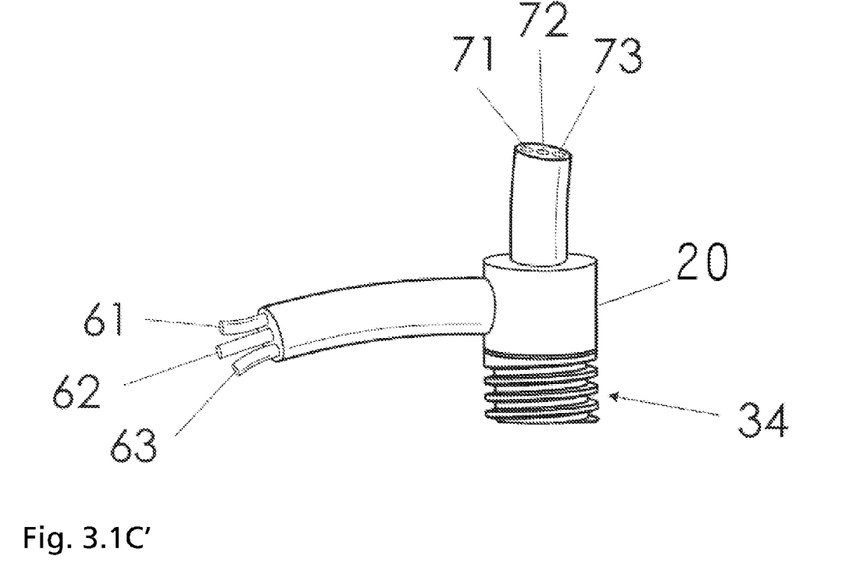
FIG. 3A is a perspective view of the bone anchored access port according to FIG. 2.
FIG. 3B is a perspective view of the bone anchored access port with one single tube line according to a second embodiment of the invention.
FIG. 3C is a perspective view of the bone anchored access port with two separate access lines but only one tube line according to a third embodiment of the invention.
Figure 3A:
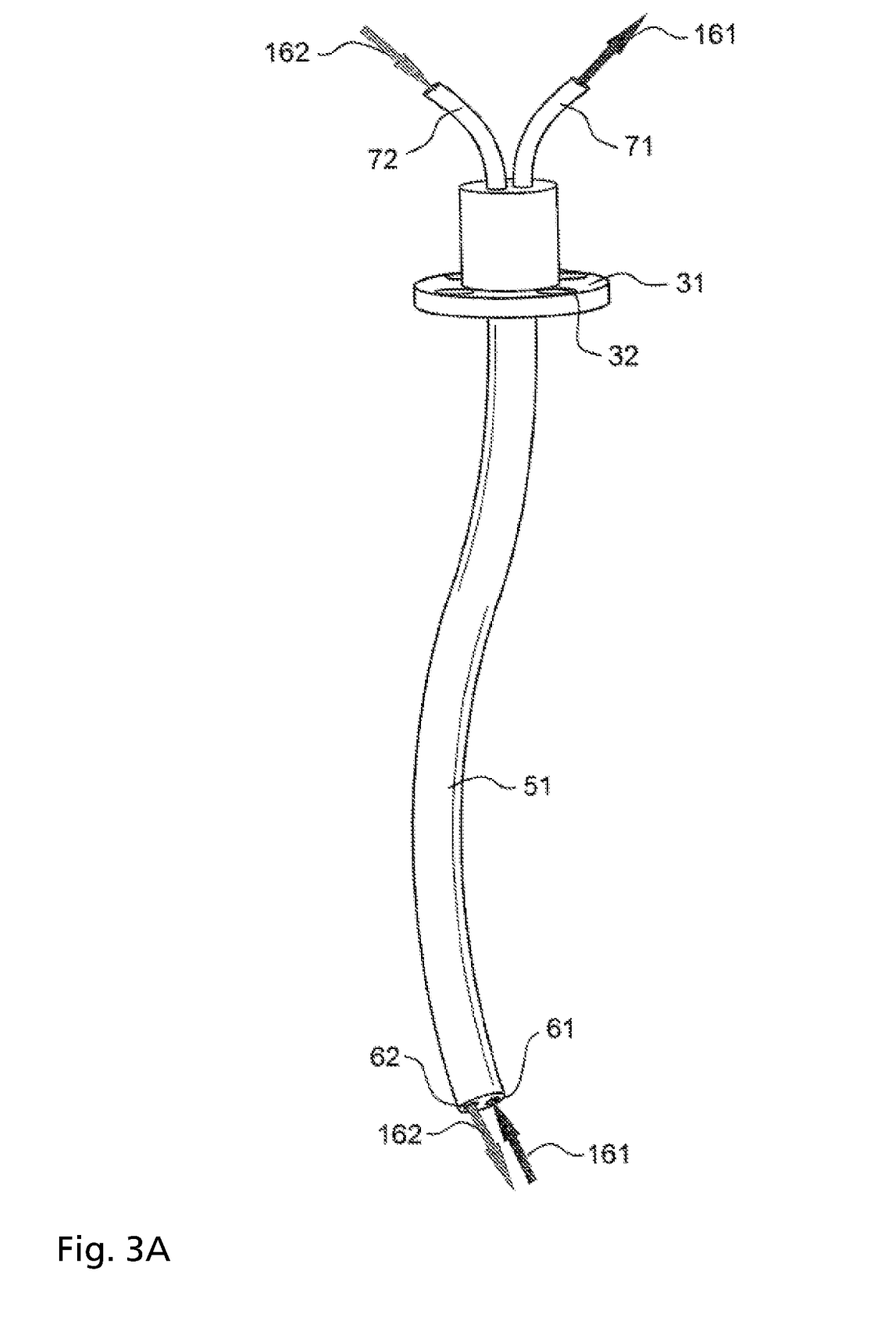

FIG. 3A is a perspective view of the bone anchored access port 10, according to FIG. 2, and illustrates one exemplary application of its use for haemodialysis. The tube lines 61 and 62, as well as the access lines 71 and 72, are shown with arrows 161 and 162 designating the flow direction of the blood. One tube line 61 and access line 71 are used for removal of blood to be dialyzed. The dialyzator is connected to the bone anchored access port 10 via an integrated pipe coupling. Dialyzed blood is returned via the second access line 72.

Figure 3B:
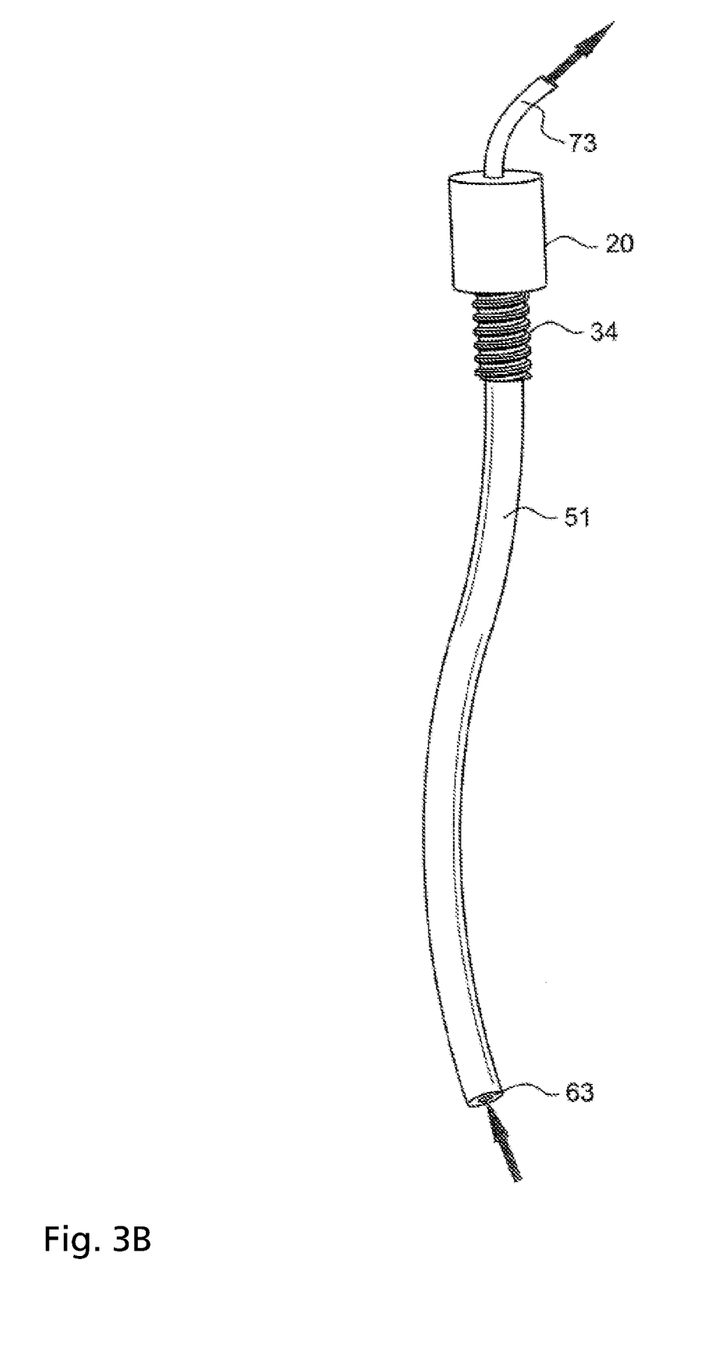

FIG. 3B is a perspective view of the bone anchored access port 10 with one single tube line 63, according to a second embodiment of the invention. An application having only one single access line 73 may be used for urinary catheterism where fluid is removed only. The difference between the first and second embodiment further resides in the fixation unit 30. The second embodiment comprises a central bone screw 34 encompassing the internal conduit 51. The fixation of the access port 10 comprises the drilling of a hole 3 in the bone 1 for introduction of the hollow fixation screw 34. The internal conduit 51 is placed in the screw 34, preferably after introduction of the latter, but it is also possible to provide a unit of screw 34 and conduit 51. Then the casing 20 comprising the actuator mechanism 40 is connected to the head of screw 34.

In a variant of the embodiment of FIG. 3B of the invention (see FIG. 3B'), the external conduit 22 of the bone anchored access port 10 comprises two separate access lines 71, 72 and the internal conduit 51 two separate tube lines 61, 62. Here, similarly to the embodiment of FIG. 2, each access line 71 or 72 has in sequence a single connector 21, a single actuator mechanism 40, and a single internal tube line 61 and 62, respectively. Although both conduits 61 and 62 are packaged in a single tube 51 they could be assembled in two independent tubes. Each access line and each tube line can have a predetermined flow direction. For example, the fluid can flow in a direction in the first access line 71 and first tube line 61 and flow in the opposite direction in the second access line 72 and second tube line 62.

In the embodiment of FIGS. 3A, 3B and 3B', the access lines 71, 72 and the tube lines 61, 62, 63 are parallel with a longitudinal axis 100 of the device 10 (see FIG. 4B). The expression "longitudinal axis 100" corresponds to a line extending lengthwise substantially symmetrically along the casing (20) and substantially perpendicular to the bone surface in which the access port is anchored.

Alternatively, the external conduit 22 and internal conduit 51 can comprise more than two separate access lines and more than two separate tube lines, respectively, in order to provide access to more than one lumen of the body. Obviously, the device can alternatively comprise more than one external conduit 22 and more than one internal conduit 51, each with one or more separate access lines or tube lines, respectively.

In the embodiment of FIG. 3B', and similarly with the embodiment of FIG. 3B, the fixation unit 34 extends axially along the longitudinal axis 100. Here, a portion of the casing 20 is used as fixation unit 34. More particularly in the example of FIG. 3B', a threaded structure is provided on the lower portion of the casing, for example, using a lathe.

Alternatively, the fixation unit 34 can consist of a roughened or, more generally, a three-dimensional structure, on at least a portion of the casing external surface. This can be provided with a mechanical treatment such as sandblasting, or using a chemical or electrochemical etching treatment or a combination of at least two of these treatments.

In order to facilitate its osseointegration, the portion of the casing 20 can also be coated with biocompatible, artificially produced bonelike substances, such as calcium sulfate or hydroxyapatite, for example, by coating the material by plasma spraying.

Figure 3C:
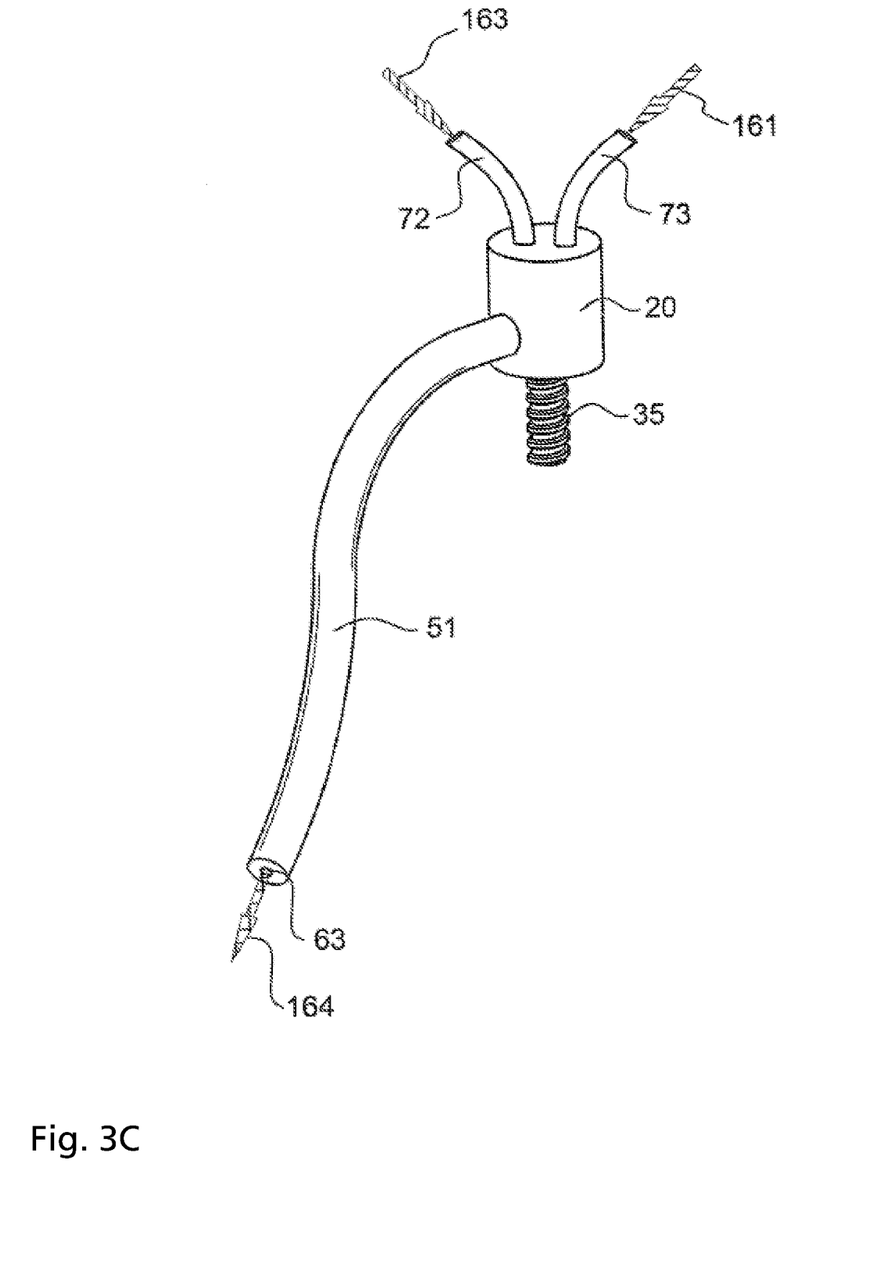

FIG. 3C is a perspective view of the bone anchored access port 10 with two separate access lines 71 and 72, but only one single tube line 63, according to a third embodiment of the invention. The access port 10, according to FIG. 3C, can be used for administration of multiple individually applied drugs, which consist of a design having two (or more) external lumens connected to the same number of external conduits or access lines 71, 72, two (or more) actuator mechanisms 40 incorporated in casing 20, followed by at least one single internal conduit 63. Thus, the arrows showing the flow direction comprise two inward directed arrows 161 and 162 and a combined flow direction arrow 164. It is clear to someone skilled in the art that the invention applies to any combination of multiple parallel access lines 71, 72 with any sequential composition of amount of internal conduits 61, 62, 63 etc., and a predetermined number of actuator mechanisms 40, preferably one for each external access line.

FIG. 3C shows a different embodiment in relation to the embodiments of FIG. 3A, 3B and 3B'. On the one hand, the fixation unit 30 uses a central single bone screw 35 in the direction of the longitudinal axis of the port. But this single screw 35 is not necessarily hollow, and any bone fixation screw according to prior art can be used, which is then connected to the casing 20 or can be produced/provided integrally with said housing 20. On the other hand, the internal conduit 51 exits the casing 20 perpendicularly to its longitudinal axis and therefore at an angle of 90 degrees in relation to the screw 35. This allows attaching the internal conduit 51 in a direction that is parallel to the upper surface of an underlying bone 1. This procedure avoids the perforation of the bone 1 and only necessitates the use of one fixation screw. It is clear that it is also possible to use several screws 33 attached to a plate like structure 31, while allowing the tubing 51 to be oriented laterally to the casing 20. Beside the shown angle of 90 degrees it is also possible to choose said angle between 70 and 110 degrees.

FIG. 3.1C' shows a variant of the embodiment of FIG. 3C where the external conduit 22 and internal conduit 51 comprise three separate access lines 71, 72, 73 and three corresponding separate tube lines 61, 62, 63, respectively. The tube lines 61, 62, 63 can provide access, for example, to a single lumen or three corresponding lumens of the body. Here, the access lines 71, 72, 73 exit the casing 20 in a direction essentially parallel with the longitudinal axis 100 of the device 10 and the tube lines 61, 62, 63, are disposed essentially perpendicular with the longitudinal axis 100, allowing for attaching the tube lines in a direction that is parallel to the upper surface of an underlying bone 1.

The tube lines 61, 62, 63, can also exit the casing 20 separately, at several locations around its periphery, for example, essentially perpendicular with the casing longitudinal axis 100. Alternatively, several tube lines can be bundled in a first internal conduit 51 while other tube lines exit the casing 20 at different locations than the first conduit, separately or bundled in a second internal conduit (not shown). For example, the other tube lines bundled in a second internal conduit can exit the casing 20 at a position opposed with the first internal conduit or making any other angle with the first internal conduit.

In a preferred embodiment, the internal conduit 51 and/or the tube lines 61, 62, 63 are placed between the skin and the bone.

In FIG. 3.1C', the fixation unit 34 is provided by a threaded structure extending over the lower portion of the casing 20, however, a single bone screw 35 can also be used. The screw can have a cylindrical shape, such as the screw shown in FIG. 3C, be have a tapered shape.

In another embodiment, a threaded support is implanted in a bone and the central screw of the casing 20 is screwed into the implanted support.

FIGS. 3.2C' shows another variant of the embodiment of FIG. 3C where the tube lines 61, 62, 63 are disposed essentially perpendicular with the longitudinal axis 100, and the access lines 71, 72, 73 exit the casing 20 making an angle of about 45° with the longitudinal axis 100. The access lines can exit the casing making any other angle between 0° and 90° with the longitudinal axis 100 as long as the access lines are able to extend through the patient's skin.

The fixation device 34, 35, as shown in FIGS. 3B, 3B', 3C, 3C.1' and 3.2C', extends axially along the longitudinal axis 100 of the device 10. The fixation unit 34, 35 can be advantageously anchored in different types of bones and/or several locations on a bone. In contrast, the plate 31 shown in FIG. 2, requires a bone having at least a flat portion in order to be stably anchored, or possibly first flattening a portion of the bone surface or modifying the plate shape according to the bone conformation, where the base 31 is fixed.

For some indications, it is favorable to use a central screw fixation or a casing with a threaded part on at least a portion of the casing instead of a bone plate in order to maximize the direct contact of skin with the underlying bone in the surrounding of the implanted device. Such direct contact minimizes the risk of infections whereas any non-biologic fixation material such as a fixation plate may be disadvantageous in such respect for certain indications.

At least one part of the fixation unit 30 is destined to be anchored to a section of the animal skeleton, such as the bony part of mastoid, hip, sternum, clavicula or others. Preferably, the fixation unit 30 is anchored to temporal bone, or more preferably to the mastoid.

Exemplary actuator mechanisms include ball valve, disk valve, such as illustrated in FIG. 4A, 4B and 5A, 5B, but also squeeze valve, gate valve, plug and the like or combinations thereof.

FIG. 4A is a cross section for one embodiment of the valve part 40 of the bone anchored port 10, according to FIG. 2, with a ball valve in closed valve position. A flat spring 41 in relaxed position actuates the ball 42 against the external conduit 22 of the bone anchored access port 10 such that the valve unit 40 is closed. Of course, other common withholding systems such as torsion spring, compression spring, spiral spring, cup spring can be used for the purpose of holding the ball 42 back in position. Although the ball valve inhibits aspiration of air or leakage of blood during manipulation, an additional plug 43 may be used when the access port 10 is unused. A protection cap 44 or any other covering device fitting over the casing 20 may be used to prevent mechanical stress or even damage, as well as external contamination; preferably a positive fit means is provided at casing 20 and cap 44 to allow a positive fit.

FIG. 4B shows the ball valve in open condition. The protection cap 44 and the plugs 43 are removed. The ball valve is initially still sealing. Afterwards, a pipe coupling 45, which is connected to the extracorporeal lumen 50, is inserted to the external conduit 22. The pipe coupling element 45 has one or several protrusions 46 at the distal end. These protrusion or pins 46 push against the ball 42 and open the actuator mechanism 40. The fluid passes between the pins 46 around the ball 42 through the valve cavity 47 into the internal conduit 51. The stress on the flat spring 41 enables repositioning of the ball 42 at the end of the external conduit 22 such that the actuator mechanism 40 is closed again. The embodiment shown in FIG. 4A and 4B comprises two different access lines 71 and 72 and tube lines 61 and 62. It is, of course, possible to use the two ball valve units to enter a common valve cavity 47 and enter one single tube line 63.

FIG. 5A is a cross section for another embodiment of the valve part of the bone anchored port 10, according to FIG. 2, with a disk valve in closed valve position. A sealing washer 141 is embedded in a base-plate being part of the casing. The base plate includes the base plate 31 for fixation, thread for the counterpiece 148 to assemble the sealing washer as well as threads of screws 142 for the counterpiece 143 of the pipe coupling. Additionally, the base plate 31 comprises a further counterpiece 143 for attachment of the internal conduit 51, counterpiece 143 being arranged under the base plate 31 and thus within a recess of the bone 1.

Figure 6:
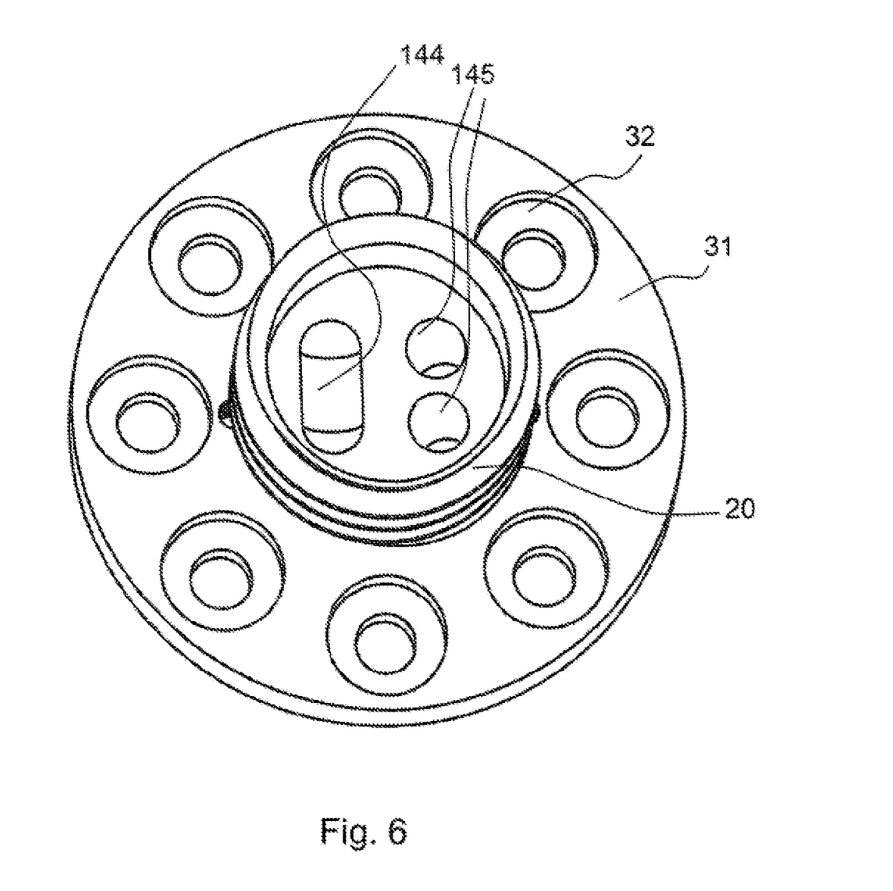
FIG. 6 is a perspective view of the base plate of the bone anchored port with a disk valve according to FIG. 5.

Relating to FIG. 6 showing a perspective view of the base plate 31 of the bone anchored port with a disk valve according to FIG. 5, a cleaning conduit 144 and two pipes 145 for end to end tubes 146 in FIG. 5A and 5B can further be seen. The sealing of the sealing washer 141 is adjusted during assembly of the counterpiece 143 to the base-plate 31. In the closed condition, according to FIG. 5A, the external conduits 22 are aligned with the cleaning conduit 144 of the disk valve. This cleaning conduit 144 short circuits both external conduits 22. This enables cleaning of the external conduit 22 in closed conditions, especially directly after and before connecting the external lumens 50. An additional plug 43 and/or even a protection cap 44, as in FIG. 4A, may be used. Both have to be removed before extracorporeal lumen 50 can be connected to the external conduit 22 via the pipe coupling 147. Opening of the disk valve is performed by turning the sealing washer 141 until the end-to-end tubes 146 and pipe 145 of the base plate 31 are aligned. End-to-end tubes 146 are thus rotated in the opening 149 within the counter piece 148 around the longitudinal axis 100 of the device 10.

The internal conduit 51 is permanently air- and waterproof attached to the casing 20. Possible pipe couplings comprise imposing a chuck cone 48 as in FIG. 4A, 4B, squeezing the internal conduit 51 with a counterpiece 143 as in FIG. 5A, 5B, gluing and the like.

The invention is suited for numerous applications in therapy, diagnosis or long-term assistance of patients suffering from various diseases or disabilities. For example, a variant of the invention can be used to perform haemodialysis.

For such application, the internal conduits 51 of the device 20 are connected to a patient's blood vessel, e.g. the internal jugular vein, subclavicular vein, vena cava. Externally, the device is connected via a tube system to a hemodialysis machine. Blood is then transferred at high flow (50-600 mL/min, or more specific 170-400 mL/min, or even more specific 220-350 mL/min) to the dialysis machine and, after purification, is returned to the patient. The stable fixation with an anchor allows the use of the port for the extended time period as 4 to 6, often 8 hours usually required for the hemodialysis treatment. After completion of the dialysis cycle the device can be closed, cleaned and capped. The port 10 can be reused many times with no need to perforate skin and vessels with needles for every single cycle. The device ac-cording to the invention is especially well suited for large voluminas as well as comprising the removal of body fluids. The diameter of lines 62, 62, 71 and 72 can be between 0.5-1.5 mm, especially between 0.7-1.2 mm, preferably around 1 mm. This enables said fluid rates of 200 to 400 ml/min with the exerted pressure, e.g. 200 mmHg, being a combination of the blood pressure of a patient and the hemodialysis pump, the pressure being applied in both directions, i.e. for removal as well as for the re-introduction of the patient's blood.

A further application refers to the continuous application of drugs that can be delivered in liquid form to any blood vessel, body lumen or organ. Such drugs may be chemotherapeutic agents for tumor therapy. The device can be used to deliver these drugs, for example, to the blood, the cerebrospinal fluid or the peritoneal cavity. Patients suffering from gastrointestinal diseases or disabilities can receive parenteral nutrition applied through the device to the blood. For diabetic patients, the administration of insulin may be facilitated because permanent access to the subcutaneous tissue is granted with this device. Simultaneous application of multiple drugs is also possible with this single device, as is depicted in FIG. 3C.

Another application may be the removal of pathologic fluid anywhere in the body, e.g. from the peritoneum in case of recurrent effusions. Also, long time urinary catheterism can be based on a device accessing the bladder. For such applications, the port can be arranged according to FIG. 3B.

Beside the mechanical valves shown in FIGS. 4 and 5, it is also possible to provide for valves working with shape memory alloy or on an electrical basis or by magnetic induction. In this context, it is possible to provide not only an on-off function for the fluid connection between internal and external conduit, but also for a controlled connection in the sense that the administration rate of a drug or the fluid flow through the lines is controlled.

While the invention has been disclosed in connection with certain preferred embodiments, this should not be taken as a limitation to the provided details. Modifications and variations of the described embodiments may be made without departing from the spirit and scope of the invention, and other embodiments should be understood to be encompassed in the present disclosure as would be understood by those of ordinary skills in the art.

LIST OF REFERENCE NUMERALS

| | |
|---|---|
| 1 | bone |
| 2 | skin |
| 3 | hole in bone |
| 10 | bone anchored access port |
| 20 | casing |
| 21 | connector |
| 22 | external conduit |
| 23 | integrated pipe coupling |
| 30 | fixation unit |
| 31 | plate |
| 32 | hole |
| 33 | bone screw |
| 34 | central bone screw |
| 35 | single bone screw |
| 40 | valve unit |
| 41 | flat spring |
| 42 | ball |
| 43 | plug |
| 44 | protection cap |
| 45 | pipe coupling |
| 46 | protrusion |
| 47 | valve cavity |
| 48 | chuck cone |
| 51 | internal conduit |
| 52 | extracorporeal lumen |
| 61 | first tube line |
| 62 | second tube line |
| 63 | third or single tube line |
| 71 | first access line |
| 72 | second access line |
| 73 | third or single access line |
| 100 | longitudinal axis |
| 141 | sealing washer |
| 142 | counter screw |
| 143 | counterpiece |
| 144 | cleaning conduit |
| 145 | pipe |
| 146 | end-to-end tube |
| 147 | pipe coupling |
| 148 | counterpiece |
| 149 | opening |
| 161 | flow direction |
| 162 | flow direction |
| 163 | flow direction |
| 164 | combined flow direction |
| 51 | internal conduit |

The invention claimed is:

1. Implantable access device for removal and/or return of fluids to a patient, being an animal or human, comprising:
a casing attached to an internal conduit to be connected with a lumen of the patient;
a connector attached at the casing and connected to an external conduit, the external conduit and/or the casing being transcutaneous, the connector being further arranged for attachment of an extracorporeal lumen to the device; and
an actuator unit within the casing to selectively allow or block the fluid communication between the internal conduit and the external conduit;
the device further comprising a fixation unit integrated in or attached at the casing arranged for fixation of the device to a bone of the patient; the fixation unit extending axially along the longitudinal axis of the device, wherein
the bone comprises the mastoid or temporal bone;
the internal conduit comprises two or more tube lines for a predetermined flow direction and the external conduit comprises two or more separate access lines for a predetermined flow direction; the tube lines exiting the casing and extending from the casing in a direction substantially parallel with the same longitudinal axis of the device that the fixation unit extends along; and
the casing is configured to be located on a surface of the mastoid or temporal bone and the casing does not pass through the surface of the mastoid or temporal bone, wherein the internal conduit is arranged to extend within the fixation unit.

2. Access device according to claim 1, wherein the fixation unit is a single, preferably central, bone screw.

3. Access device according to claim 2, wherein the bone screw is a hollow bone screw accommodating the portion of the internal conduit near the casing.

4. Access device according to claim 1, wherein at least a portion of the casing is used as a fixation unit.

5. Access device according to claim 4, wherein the fixation unit is a threaded structure provided on the lower portion of the casing.

6. Access device according to claim 4, wherein the fixation unit is a roughened or a three-dimensional structure provided on the lower portion of the casing.

7. Access device according to claim 1, wherein the portion of the internal conduit near the casing is attached essentially perpendicular to said longitudinal axis of the device.

8. Access device according to claim 1, wherein the access lines exit the casing in a direction essentially parallel with the longitudinal axis of the device or with an angle comprised between 0° and 90° with the longitudinal axis of the device.

9. Access device according to claim 1, wherein the access lines exit the casing with an angle of about 45° with the longitudinal axis of the device.

10. Access device according to claim 1, wherein access line and tube line have an outward flow direction and the second access line and tube line have an inward flow direction.

11. Access device according to claim 1, wherein the internal conduit comprises a single tube line being able to combine the inward flow of the access lines of the external conduit.

12. Access device according to claim 1, wherein the internal conduit comprises three tube lines and the external conduit comprises three separate access lines.

13. Access device according to claim 1, wherein the tube lines and/or access lines are provided in single tubing or are arranged in a bundle of separate conduits.

14. Access device according to claim 1, wherein said tube lines exit the casing separately, at several locations around its periphery.

15. Access device according to claim 1, wherein the internal conduit and/or the tube lines are arranged such as to be between the skin and the bone.

16. Access device according to claim 1, wherein the actuator unit is a valve connected on one hand to each tube line of said internal conduit and on the other hand to each access line of said external conduit.

17. Access device according to claim 16, wherein the valve unit comprises a number of ball valve units or disk valve units equal to the greater number of tube lines and access lines.

18. Access device according to claim 5, wherein said threaded structure being arranged such as to maximize direct contact of skin with the underlying bone in the surrounding of the implanted device.

19. Access device according to claim 1, wherein the fixation unit comprises a plate, said plate comprising at least one through hole, wherein said at least one through hole is configured to enable a fixation means to attach said plate to said mastoid or temporal bone of a patient.

20. An implantable access device for removal and/or return of fluids to a patient, being an animal or human, comprising:
    a casing attached to an internal conduit to be connected with a lumen of the patient;
    a connector attached at the casing and connected to an external conduit, the external conduit and/or the casing being transcutaneous, the connector being further arranged for attachment of an extracorporeal lumen to the device; and
    an actuator unit within the casing to selectively allow or block the fluid communication between the internal conduit and the external conduit;
    the device further comprising a fixation unit integrated in or attached at the casing arranged for fixation of the device to a bone of the patient; the fixation unit extending axially along the longitudinal axis of the device; the fixation unit comprising a plate which comprises a plurality of apertures defined therein that are each configured to receive a fastener to fix the device to the bone, wherein
    the bone comprises the mastoid or temporal bone;
    the internal conduit comprises two or more tube lines for a predetermined flow direction and the external conduit comprises two or more separate access lines for a predetermined flow direction; the tube lines exiting the casing in a direction substantially parallel with the longitudinal axis of the device; and
    the casing is configured to be located on a surface of the mastoid or temporal bone and the casing does not pass through the surface of the mastoid or temporal bone,
    wherein the internal conduit is arranged to extend within the fixation unit.

* * * * *